United States Patent
Yoshida et al.

(10) Patent No.: US 8,641,626 B2
(45) Date of Patent: Feb. 4, 2014

(54) ULTRASONIC DIAGNOSIS APPARATUS AND ULTRASONIC DIAGNOSIS METHOD

(75) Inventors: Tetsuya Yoshida, Nasushiobara (JP); Naohisa Kamiyama, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 647 days.

(21) Appl. No.: 11/280,326

(22) Filed: Nov. 17, 2005

(65) Prior Publication Data
US 2006/0116582 A1 Jun. 1, 2006

(30) Foreign Application Priority Data
Nov. 22, 2004 (JP) ................. 2004-337647

(51) Int. Cl.
*A61B 8/00* (2006.01)
(52) U.S. Cl.
USPC ............ 600/458; 600/407; 600/437; 600/443
(58) Field of Classification Search
USPC .................. 600/407, 437, 443, 458
See application file for complete search history.

(56) References Cited

U.S. PATENT DOCUMENTS

| | | | |
|---|---|---|---|
| 5,694,937 A * | 12/1997 | Kamiyama | 600/443 |
| 5,944,666 A | 8/1999 | Hossack et al. | |
| 6,080,107 A * | 6/2000 | Poland | 600/458 |
| 6,186,951 B1 * | 2/2001 | Lizzi et al. | 600/458 |
| 6,245,019 B1 | 6/2001 | Kamiyama | |
| 6,340,348 B1 * | 1/2002 | Krishnan et al. | 600/447 |
| 2004/0215076 A1 | 10/2004 | Kamiyama | |
| 2005/0203406 A1 | 9/2005 | Kamiyama | |

FOREIGN PATENT DOCUMENTS

| | | |
|---|---|---|
| JP | 8-196537 A | 8/1996 |
| JP | 11-155858 | 6/1999 |
| JP | 11-253449 A | 9/1999 |
| JP | 11-318901 | 11/1999 |
| JP | 2001-252270 A | 9/2001 |
| JP | 2001-269341 A | 10/2001 |
| JP | 2002-224108 A | 8/2002 |
| JP | 2002-360576 A | 12/2002 |
| JP | 2004-321688 A | 11/2004 |
| JP | 2005-237738 | 9/2005 |

OTHER PUBLICATIONS

Japanese Office Action mailed Sep. 28, 2010 in corresponding Japanese Application No. 2004-337647 (with English Translation).

* cited by examiner

*Primary Examiner* — Peter Luong
(74) *Attorney, Agent, or Firm* — Oblon, Spivak, McClelland, Maier & Neustadt, L.L.P.

(57) ABSTRACT

An ultrasonic diagnostic apparatus comprises a transmitting and receiving section which transmits and receives a first ultrasonic wave that has such a sound pressure as practically does not destroy a contrast agent bubble given to a subject and that is for obtaining a bloodstream circulating image about a target area of the subject and which transmits a second ultrasonic wave that has such a sound pressure as destroys the contrast agent bubble and that is for causing the contrast agent bubble passing through a part of the target area to disappear from the circulating image, a timing specify section which informs the transmitting and receiving section of the timing of the transmission of the second ultrasonic wave, an image generating section which generates an ultrasonic image on the basis of each signal obtained by the transmission and reception of the first ultrasonic wave.

28 Claims, 10 Drawing Sheets

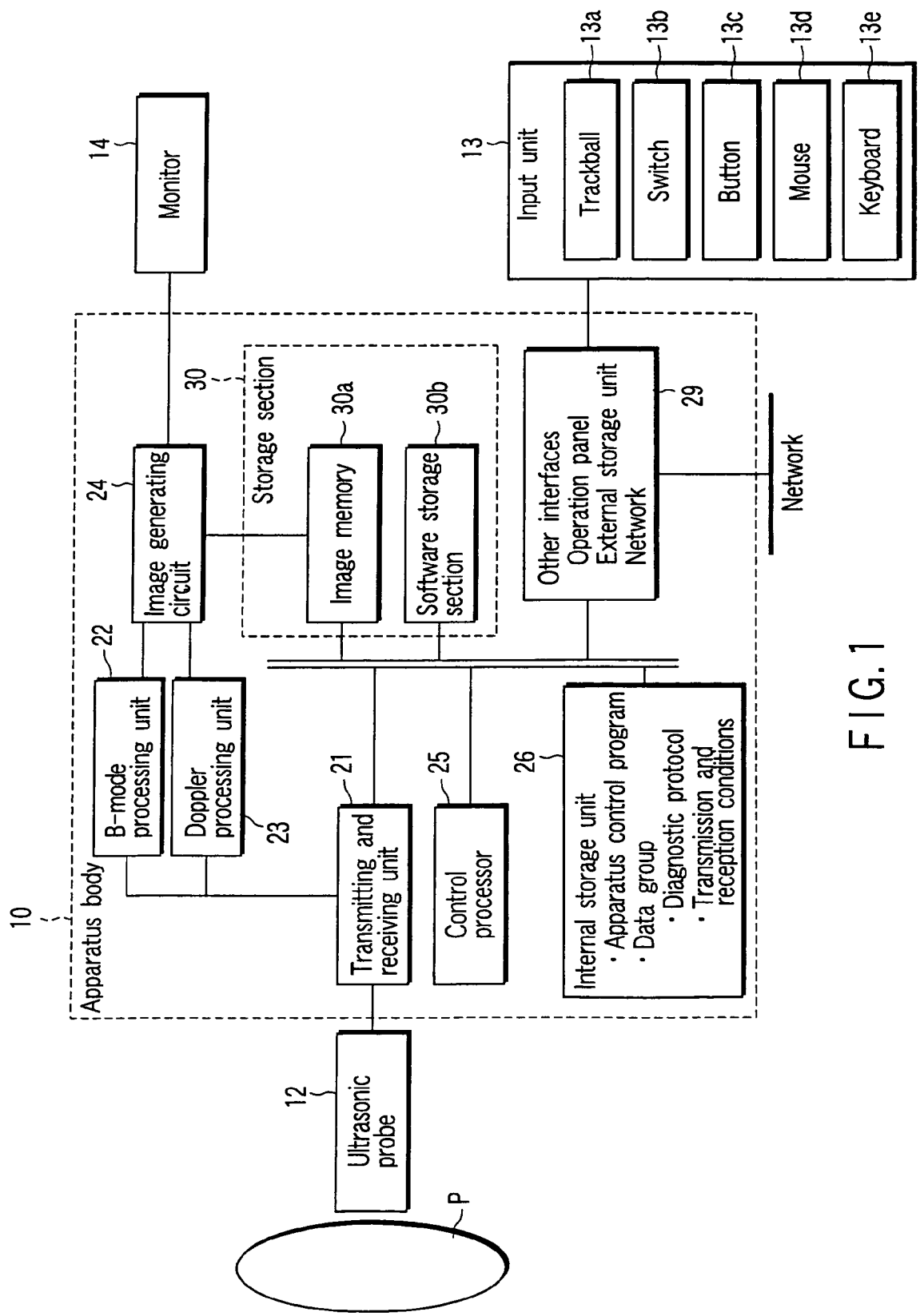
F I G. 1

ULTRASONIC DIAGNOSIS APPARATUS AND ULTRASONIC DIAGNOSIS METHOD

CROSS-REFERENCE TO RELATED APPLICATIONS

This application is based upon and claims the benefit of priority from prior Japanese Patent Application No. 2004-337647, filed Nov. 22, 2004, the entire contents of which are incorporated herein by reference.

BACKGROUND OF THE INVENTION

1. Field of the Invention

This invention relates to an ultrasonic diagnostic apparatus and an ultrasonic diagnostic method which are capable of providing diagnostic information about a microscopic bloodstream circulation on a capillary level and a microscopic structure of vascular flow faster than in a capillary in an angiographic echo method using an ultrasonic contrast agent.

2. Description of the Related Art

In ultrasonic diagnosis, heartbeats or the movement of the baby in the womb can be displayed in real time by a simple operation of just applying an ultrasonic probe to the surface of the body. Since ultrasonic diagnosis requires no X rays, it ensures a high safety and can be used in obstetrical service, home care service at home, or the like. Moreover, since an apparatus used in ultrasonic diagnosis is smaller in size than such a diagnostic apparatus as an X-ray apparatus, an X-ray CT scanner, or an MRI machine, bedside examination can be made easily. Accordingly, ultrasonic diagnosis has many advantages.

With the recent commercialization of an intravenous-dosage ultrasonic contrast agent, an angiographic echo method has been used in examining the heart or liver. The angiographic echo method is to enhance a bloodstream signal by injecting an ultrasonic contrast agent into a vein and then evaluate the hemodynamic stability.

In most contrast agents, microbubbles function as an ultrasonic reflection source. Since bubbles are easily destroyed by the mechanical action of an ultrasonic wave because of their delicate base material, even if the ultrasonic wave is irradiated at the normal diagnosis level, the intensity of the signal from the scanning surface decreases.

Therefore, to observe a dynamic behavior of a return current in real time, it is necessary to reduce the destruction of bubbles due to scanning by, for example, lowering the sound pressure of ultrasonic wave. However, when a low-sound-pressure ultrasonic wave is used, the signal-to-noise (S/N) ratio decreases. Therefore, signal processing to compensate for the decrease is needed.

Making use of the characteristic of bubble destruction, the following method has been devised. First, a low-sound-pressure ultrasonic wave is transmitted and received, thereby visualizing the moving state of bubbles flowing into the scanning surface. Next, the transmission and reception of the low-sound-pressure ultrasonic wave are stopped. A high-sound-pressure ultrasonic wave transmitted after the stop destroys all of the bubbles existing at the scanning surface (precisely, in the irradiated volume). Then, the transmission of the high-sound-pressure ultrasonic wave is stopped. A low-sound-pressure ultrasonic wave retransmitted and re-received visualizes bubbles flowing into the scanning surface. This method is known as a replenishment method (for example, refer to Jpn. Pat. Appln. KOKAI Publication No. 11-155858).

Ultrasonic images are treated as two-dimensional images. Actually, however, ultrasonic waves are transmitted in a plurality of directions. On the basis of a plurality of pieces of one-dimensional information acquired from the respective directions, a two-dimensional image is created.

In recent years, a method has been developed which limits the transmission area of high-sound-pressure ultrasonic waves to a local range and destroys only the bubbles in the local area of the diagnostic image. In this method, of the blood vessel images drawn in the diagnostic image, only the bubbles flowing through the desired blood vessel selectively disappear. However, even when only the bubbles in the local area of the diagnostic image had been destroyed, an image reflecting the speed and amount of the contrast agent flowing through the individual blood vessels could not be obtained.

BRIEF SUMMARY OF THE INVENTION

It is an object of the present invention to provide an ultrasonic diagnostic apparatus and an ultrasonic diagnostic method which are capable of creating a diagnostic image that reflects the speed and amount of a contrast agent flowing through the individual blood vessels in diagnosis at a microscopic vascular bifurcation level.

To achieve the object, an ultrasonic diagnostic apparatus and an ultrasonic diagnostic method according to the present invention are configured as follows:

(1) An ultrasonic diagnostic apparatus which obtains a diagnostic image by scanning with an ultrasonic wave a target area of a subject to whom a contrast agent bubble has been given, the ultrasonic diagnostic apparatus comprising: an ultrasonic probe which is brought into contact with the target area; a transmitting and receiving section which transmits and receives via the ultrasonic probe a first ultrasonic wave that has such a sound pressure as does not practically destroy the contrast agent bubble and that is for obtaining a bloodstream circulating image about the target area and which transmits a second ultrasonic wave that has such a sound pressure as destroys the contrast agent bubble and that is for causing the contrast agent bubble passing through a part of the target area to disappear from the circulating image; a timing specify section which informs the transmitting and receiving section of the timing of the transmission of the second ultrasonic wave; an image generating section which generates a plurality of ultrasonic images on the basis of a plurality of received signals obtained by the transmission and reception of the first ultrasonic wave; and a display section which displays the diagnostic image on the basis of the plurality of ultrasonic images generated by the image generating section.

(2) In the ultrasonic diagnostic apparatus written in item (1), the timing specify section instructs the transmitting and receiving section to execute or stop the transmission of the second ultrasonic wave for an arbitrary time, and the arbitrary time falls with a period during which a discontinuous part of the contrast agent bubble formed by the transmission of the second ultrasonic wave is seen in the diagnostic and remains in the target area.

(3) In the ultrasonic diagnostic apparatus written in item (2), the arbitrary time is 0.01 second to 5 seconds.

(4) The ultrasonic diagnostic apparatus written in item (2) further comprises a setting section which sets at least one of the arbitrary time and the number of executions or stops of the transmission of the second ultrasonic wave.

(5) The ultrasonic diagnostic apparatus written in item (2) further comprises an image processing section which generates a plurality of difference images, each difference image is obtained by using a first image generated before the transmission of the second ultrasonic wave is executed or stopped for the arbitrary time and a second image generated after the transmission of the second ultrasonic wave is executed or stopped for the arbitrary time among a plurality of ultrasonic images generated by the image generating section and performing a difference operation in luminance on each position on the first image and on the corresponding position on the second image.

(6) In the ultrasonic diagnostic apparatus written in item (5), the image processing section, using said plurality of difference images, performs at least one of a maximum retention operation, a minimum retention operation, an integral operation, and an average operation in luminance on each of the positions corresponding to one another on the individual difference images.

(7) In the ultrasonic diagnostic apparatus written in item (5), the display section displays the first image and the difference image in a superimposing manner.

(8) In the ultrasonic diagnostic apparatus written in item (7), the display section displays the first image and the difference image in different colors.

(9) The ultrasonic diagnostic apparatus written in item (1) further comprises a setting section for setting a range to which the second ultrasonic wave is transmitted.

(10) In the ultrasonic diagnostic apparatus written in item (1), the transmitting and receiving section transmits a third ultrasonic wave which has a sound pressure that destroys the contrast agent bubble to the whole of the target area before transmitting the second ultrasonic wave.

(11) In the ultrasonic diagnostic apparatus written in item (10), the timing specify section informs the transmitting and receiving section of the timing of the transmission of the third ultrasonic wave.

(12) In the ultrasonic diagnostic apparatus written in item (1), the transmitting and receiving section executes the transmission and reception of the first ultrasonic wave and the second transmission three-dimensionally a plurality of times, and the image generating section generates a plurality of three-dimensional images or two-dimensional projected images on the basis of a plurality of received signals obtained by the transmission and reception of the first ultrasonic wave.

(13) An ultrasonic diagnostic method of obtaining a diagnostic image by scanning with an ultrasonic wave a target area of a subject to whom a contrast agent bubble has been given, the ultrasonic diagnostic method comprising: transmitting and receiving to and from the subject a first ultrasonic wave that has such a sound pressure as does not practically destroy the contrast agent bubble and that is for obtaining a bloodstream circulating image about the target area; transmitting to the subject with a arbitrarily specified timing a second ultrasonic wave that has such a sound pressure as destroys the contrast agent bubble and that is for causing the contrast agent bubble passing through a part of the target area to disappear from the circulating image; generating a plurality of ultrasonic images on the basis of a plurality of received signals obtained by the transmission and reception of the first ultrasonic wave; and a displaying the diagnostic image on the basis of said plurality of ultrasonic images.

(14) In the ultrasonic diagnostic method written in item (13), the transmission of the second ultrasonic wave is executed or stopped for an arbitrary time, and the arbitrary time falls with a period during which a discontinuous part of the contrast agent bubble formed by the transmission of the second ultrasonic wave is seen in the diagnostic image and remains in the target area.

(15) In the ultrasonic diagnostic method written in item (14), the arbitrary time is 0.01 second to 5 seconds.

(16) In the ultrasonic diagnostic method written in item (14), at least one of the arbitrary time and the number of executions or stops of the transmission of the second ultrasonic wave is set arbitrarily.

(17) In the ultrasonic diagnostic method written in item (14), a plurality of difference images are generated, each difference image is obtained by using a first image generated before the transmission of the second ultrasonic wave is executed or stopped for the arbitrary time and a second image generated after the transmission of the second ultrasonic wave is executed or stopped for the arbitrary time among said plurality of ultrasonic images and performing a difference operation in luminance on each position on the first image and on the corresponding position on the second image.

(18) In the ultrasonic diagnostic method written in item (17), at least one of a maximum retention operation, a minimum retention operation, an integral operation, and an average operation in luminance is performed on each of the positions corresponding to one another on the individual difference images, using said plurality of difference images.

(19) In the ultrasonic diagnostic method written in item (17), the first image and the difference image are displayed in a superimposing manner.

(20) In the ultrasonic diagnostic method written in item (19), the first image and the difference image are displayed in different colors.

(21) In the ultrasonic diagnostic method written in item (13), the range to which the second ultrasonic wave is transmitted is set arbitrarily.

(22) In the ultrasonic diagnostic method written in item (13), a third ultrasonic wave which has a sound pressure that destroys the contrast agent bubble is transmitted to the whole of the target area before the second ultrasonic wave is transmitted.

(23) In the ultrasonic diagnostic method written in item (22), the timing of the transmission of the third ultrasonic wave is set arbitrarily.

(24) In the ultrasonic diagnostic method written in item (13), the transmission and reception of the first ultrasonic wave and the transmission of the second ultrasonic wave are executed three-dimensionally a plurality of times, and a plurality of three-dimensional images or two-dimensional projected images are generated on the basis of a plurality of received signals obtained by the transmission and reception of the first ultrasonic wave.

According to the present invention, an image reflecting the speed and amount of the contrast agent flowing through the individual blood vessels is obtained in diagnosis at a microscopic vascular bifurcation level.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a block diagram of an ultrasonic diagnostic apparatus according to a first embodiment of the present invention;

DETAILED DESCRIPTION OF THE INVENTION

Figure 2A:
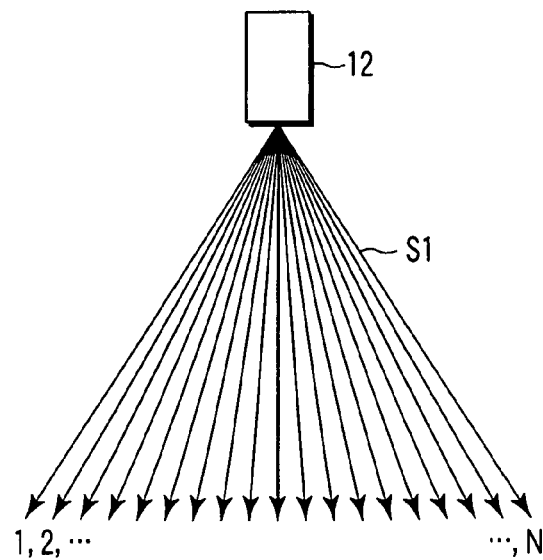
FIG. 2A schematically shows a transmission and reception form of an ultrasonic pulse in the first embodiment.

Hereinafter, referring to the accompanying drawings, a first to a fourth embodiment of the present invention will be explained.

(First Embodiment)

First, a first embodiment of the present invention will be explained.

[Configuration of Ultrasonic Diagnostic Apparatus]

FIG. 1 is a block diagram of an ultrasonic diagnostic apparatus according to a first embodiment of the present invention.

As shown in FIG. 1, the ultrasonic diagnostic apparatus of the first embodiment comprises an apparatus body 10, an ultrasonic probe 12, an input unit 13, and a monitor (or display section) 14.

The apparatus body 10 includes a transmitting and receiving unit (or transmitting and receiving section) 21, a B-mode processing unit 22, a Doppler processing unit 23, an image generating circuit (or image generating section) 24, a control processor (or image processing section) 25, an internal storage unit 26, an interface 29, and a storage section 30.

These transmitting and receiving unit 21, B-mode processing unit 22, Doppler processing unit 23, image generating circuit 24, control processor 25, internal storage unit 26, interface 29, and storage section 30 may be composed of such hardware as an integrated circuit or may be a modularized software program.

The transmitting and receiving unit 21 includes a pulser circuit, a delay circuit, and a trigger generator circuit. The pulser circuit generates repeatedly a rate pulse to form transmission ultrasonic waves at a specific rate frequency fr [Hz] (period: 1/fr second). The delay circuit converges transmission ultrasonic waves into a beam channel by channel and gives a delay time necessary to determine transmission directivity to each rate pulse, thereby producing an ultrasonic pulse used to scan a subject P. The direction in which ultrasonic pulses are transmitted to the surface of the transducer of the ultrasonic probe 12 is adjusted by changing the delay time. The trigger generator circuit applies a driving pulse to the ultrasonic probe 12 with the timing based on the rate pulse.

The transmitting and receiving unit 21 has the function of executing a scan sequence (explained later) according to an instruction given by the control processor 25. This function includes the function of changing the delay time, transmission frequency, transmission driving voltage, and others instantaneously. The change of the transmission driving voltage is particularly realized by a liner-amplifier-type transmission circuit capable of changing its value instantaneously or the mechanism of switching a plurality of power supply units electrically.

The transmitting and receiving unit 21 further includes an amplifier circuit, an A/D converter, and an adder. The amplifier circuit amplifies an echo signal (explained later) taken in from the ultrasonic probe 12 on a channel basis. The A/D converter gives a delay time necessary to determine reception directivity to the amplified echo signals. The adder adds the echo signals to which the delay times have been given. This addition emphasizes the reflected components from the directions corresponding to the reception directivities of the echo signals. This produces a comprehensive beam of ultrasonic transmission and reception which has a reception directivity and a transmission directivity.

The B mode processing unit 22 generates data in which a signal intensity is expressed in luminance by subjecting the echo signal received from the transmitting and receiving unit 21 to logarithmic amplification, envelope detection, and others. The data is sent to the image generating circuit 24 and is displayed on the monitor 14 as a B-mode image in which the intensity of the reflected wave is represented in luminance.

The Doppler processing unit 23 frequency-analyzes speed information on the basis of the echo signal received from the transmitting and receiving unit 21, extracts the echo component of the bloodstream, tissue, and contrast agent, and obtains bloodstream information on the average speed, dispersion, power, and others at many points. The bloodstream information is sent to the image generating circuit 24 and is displayed in color as an average speed image, a dispersion image, a power image, and an image combining these on the monitor 14.

The image generating circuit 24 converts a scanning line signal string obtained by scanning into a scanning line signal string in a video format as found in television, thereby generating an ultrasonic image. The image generating circuit 24 further includes a storage memory to store image data. This enables the operator to call up the image recorded during examination after, for example, diagnosis.

The control processor 25, which functions as an information processing unit, controls all of the operations of the ultrasonic diagnostic apparatus in the first embodiment. The control processor 25 particularly reads from the internal storage unit 26 a control program for executing ultrasonic transmission and reception, image generation, image display, scan sequence (explained later), difference operation, maximum retention operation, average operation, integral operation, superimpose display, and others, develops the control program on a software storage section 30b, and performs operations on and control of various processes.

The internal storage unit 26 stores not only a control program for executing ultrasonic transmission and reception, image generation, image display, scan sequence, difference operation, maximum retention operation, average operation, integral operation, superimpose display, and others, but also diagnostic information (e.g., patient IDs and doctor's remarks), diagnostic protocol, transmission and reception conditions, and other data groups. Moreover, the internal storage unit 26 is used to keep the image data memorized in the image memory 30a, if necessary. The data kept in the internal storage unit 26 can be transferred to an external peripheral unit by way of the interface 29.

The interface 29 is connected to the input unit 13, a network, and others. In addition, the interface 29 is connected to a new external storage unit (not shown) as needed. The data, including ultrasonic images, or the result of analysis and the like obtained by the ultrasonic diagnostic apparatus can be transferred to another unit via the interface 29 and network.

The storage section 30 includes an image memory 30a and a software storage section 30b. The image memory 30a is a storage memory which stores the image data received from the image generating circuit 24. The operator can call up the image data, for example, after diagnosis. The called image data is displayed in still image form or reproduced in moving image form. When the image data is reproduced in moving image form, a plurality of items of image data are used. The image memory 30a stores the output signal (referred to as an RF signal) of the transmitting and receiving unit 21, the output signal of the B-mode processing unit 22, other raw data, or image data acquired through the network as needed. When ultrasonic transmission and reception, image generation, image display, scan sequence, difference operation, maximum retention operation, average operation, integral operation, superimpose display, or the like is executed, the software storage section 30b temporarily stores a control program necessary to execute these operations.

The ultrasonic probe 12 includes a plurality of piezoelectric vibrators that convert the reflected wave from the subject P into an electric signal, an acoustic matching layer that acoustically matches the piezoelectric vibrators with the subject P, and a backing material that absorbs ultrasonic waves propagating from the piezoelectric vibrators toward behind the ultrasonic probe 12. The ultrasonic probe 12 generates ultrasonic pulses on the basis of a driving signal from the transmitting and receiving unit 21.

When an ultrasonic pulse is transmitted from the ultrasonic probe 12 to the subject P, the ultrasonic pulse is reflected in succession at the discontinuous parts of the acoustic impedance in the subject P. The ultrasonic pulse returned from the inside of the subject is received as an echo signal by the ultrasonic probe 12. The amplitude of the echo signal depends on the difference between the acoustic impedances at the discontinuous parts at which the pulse was reflected. In addition, when the transmitted ultrasonic pulse is reflected at a moving body, such as the bloodstream or the heart wall, the echo signal is subjected to frequency shift by the Doppler effect according to the speed component of the moving body in the direction in which the ultrasonic pulse is transmitted.

The input unit 13, which is connected to the apparatus body 10, is used to input to the apparatus body 10 various instructions from the operator, conditions, an instruction to set a region of interest (ROI), various image quality condition setting instructions, and others. The input unit 13 includes a trackball (or setting section) 13a, various switches 13b, a button (or a timing specify section) 13c, a mouse (or setting section) 13d, and a keyboard (or setting section) 13e.

The button 13c is used not only to instruct the start of a scan sequence but also to specify the timing of stopping the transmission of a high-sound-pressure ultrasonic pulse (hereinafter, referred to as a local destruction high-sound-pressure pulse). In place of the button 13c, the switches 13b may be used.

The trackball 13a is used to set the transmission direction D of a local destruction pulse high-sound-pressure pulse. The mouse 13d is used to set the transmission range R of a local destruction high-sound-pressure pulse, the stop time (an arbitrary length of time) of a local destruction high-sound-pressure pulse, the number of stops of a local destruction high-sound-pressure pulse, the interval between stop periods, and others. In place of the mouse 13d, the keyboard 13e may be used. A touch command screen is generally used as the switch 13b. The functions of the trackball 13a, button 13c, mouse 13d, and keyboard 13e can be realized by a touch command screen.

The monitor 14 displays morphologic information and bloodstream information on the inside of the subject P in the form of diagnostic images on the basis of the scanning line signal string in the video format obtained by the image generating circuit 24.

[Use of Ultrasonic Diagnostic Apparatus]
(Assumption)

In the first embodiment, a so-called "next-generation contrast agent" is used as a contrast agent given to the subject P. The "next-generation contrast agent" has the property of preventing bubbles from being destroyed even when a low-sound-pressure ultrasonic pulse (hereinafter, referred to as a "low-sound-pressure pulse") is transmitted and continuing emitting a harmonic signal. Therefore, use of a next-generation contrast agent enables prolonged visualization. A constant infusion pump is used to inject a contrast agent. This makes the amount of contrast agent given to the subject in a specific time minute and constant, which keeps the concentration of the contrast agent in the body of the subject constant for a long time.

(Transmission Form of Ultrasonic Pulses)

FIG. 2A schematically shows a transmission and reception form of an ultrasonic pulse in the first embodiment.

As shown in FIG. 2A, when a normal B-mode image is generated, an ultrasonic pulse is transmitted and received an N number of times. Then, on the basis of an N number of scanning lines S1 obtained from the N number of transmissions and receptions, one frame of ultrasonic image is generated. There is a method of obtaining scanning-line information for a single line by transmitting and receiving an ultrasonic pulse in one direction repeatedly. This method has the same purpose as that of the above method in generating a B-mode image. Therefore, its explanation will be omitted.

Figure 2B:
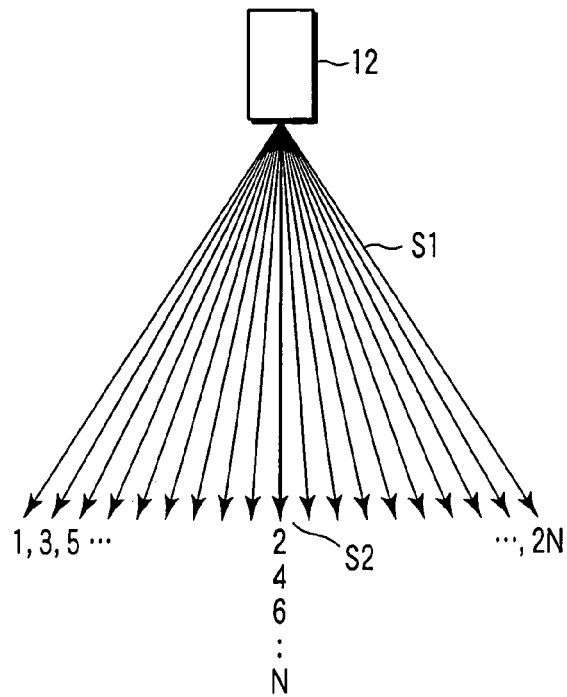
FIG. 2B schematically shows another transmission and reception form of an ultrasonic pulse in the first embodiment.

FIG. 2B schematically shows another transmission and reception form of an ultrasonic pulse in the first embodiment.

When a B-mode image and an M-mode image are generated at the same time, the transmission and reception of an ultrasonic pulse to generate a B-mode image and the transmission and reception of an ultrasonic pulse to generate an M-mode image are performed an N number of times alternately as shown in FIG. 2B. On the basis of an N number of scanning lines S1 obtained from the N number of transmissions and receptions for a B-mode image, one frame of ultrasonic image is generated. Moreover, on the basis of an N number of scanning lines S2 obtained from the N number of transmissions and receptions for an M-mode image, information on a change in the time of the echo signal is generated.

In this case, if the rate frequency (the number of transmissions and receptions of an ultrasonic pulse performed in 1 [sec]) is fr [Hz], a B-mode image is generated at a rate of one image in 2N/fr [sec]. Since an M-mode image is generated by a received signal obtained at a rate of one image in 2N/fr [sec], information following a very fast movement can be provided.

While in the first embodiment, the direction in which an M-mode image ultrasonic pulse is transmitted and received is perpendicular to the surface of the transducer of the ultrasonic probe 12, the present invention is not limited to this. Moreover, although the ultrasonic transmission and reception of a B-mode image are alternated with the ultrasonic transmission and reception of an M-mode image, their ratio can be changed arbitrarily.

(Drawing a Vascular Structure With a Low-Sound-Pressure Pulse)

Figure 3:
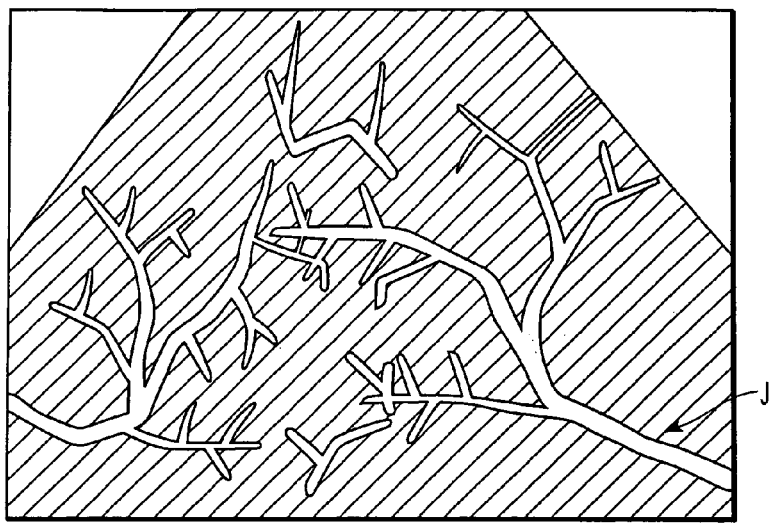
FIG. 3 shows an ultrasonic image created by the transmission and reception of a low-sound-pressure pulse in the first embodiment.

FIG. 3 shows an ultrasonic image generated as a result of the transmission and reception of a low-sound-pressure pulse in the first embodiment.

In the first embodiment, first, the subject P is scanned with a low-sound-pressure pulse (or a first ultrasonic wave). As described above, in the first embodiment, a "next-generation contrast agent" having the aforementioned property is used as a contrast agent given to the subject P. Therefore, when the subject P is scanned with a low-sound-pressure pulse, almost all of the vascular structure in the scanning surface is drawn in an ultrasonic image.

(Parameter Setting)

Figure 4A:
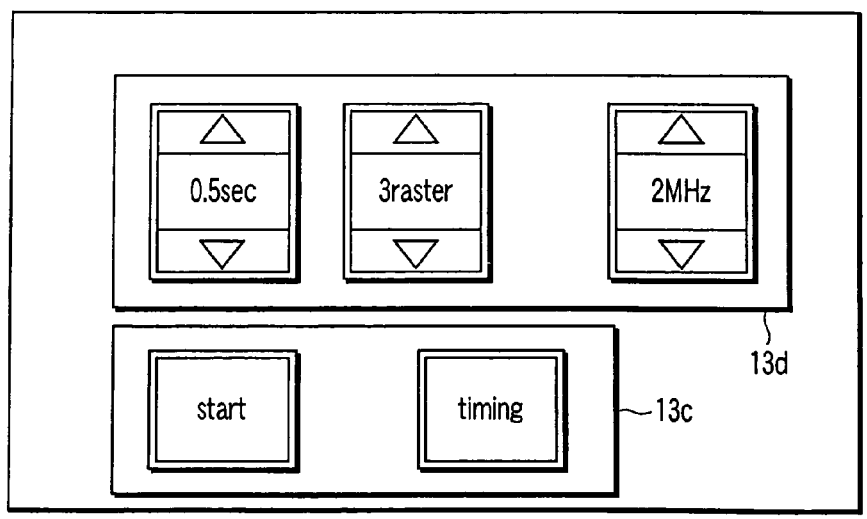
FIG. 4A schematically shows buttons and a mouse in the first embodiment.
Figure 4B:
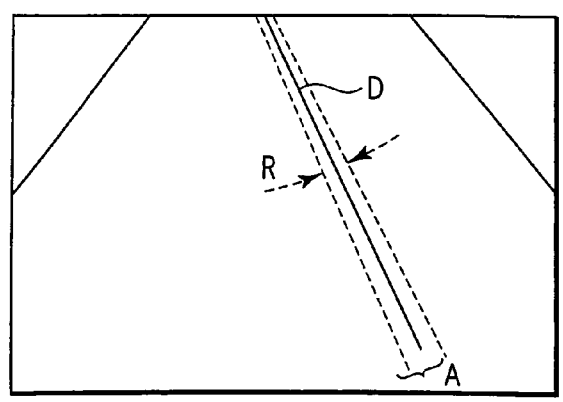
FIG. 4B is a conceptual diagram to help explain parameter setting in the first embodiment.

FIG. 4A schematically shows a button 13c and a mouse 13d in the first embodiment. FIG. 4B is a conceptual diagram to help explain parameter setting in the first embodiment.

After a vascular structure is drawn in an ultrasonic image, the operator operates the trackball 13a, mouse 13d, keyboard 13e, or touch command screen, while looking at the vascular structure, thereby setting the necessary parameters to execute a scan sequence.

The parameters include the stop time of the transmission of a local destruction high-sound-pressure pulse, the transmission frequency of the local destruction high-sound-pressure pulse, the transmission direction D of the local destruction high-sound-pressure pulse, and the transmission range R of the local destruction high-sound-pressure pulse. In the parameter setting, it is important to point the transmission direction D of the local destruction high-sound-pressure pulse at the main part of the target blood vessel and set the stop time of the transmission of the local destruction high-sound-pressure pulse according to the blood velocity of the target blood vessel.

This is because the blood velocity differs greatly, depending on the types of blood vessels. For example, the blood velocity in the hepatic artery is about 20 [cm/sec] and the blood velocity in the portal vein is about 10 [cm/sec]. In the case of peripheral blood vessels, the blood velocity may be faster. Therefore, when the same stop time is set for all of the blood vessels, a blob bubble b (explained later) differs in length between the blood vessels.

In this situation, the inventor assumed that the target blood velocity was about 5 [cm/sec] to 30 [cm/sec] and took visibility and the degree of diffusion into account. As a result, the inventor came to the conclusion that the length of a blob bubble b was preferably about 0.3 [cm] to 10 [cm]. According to this conclusion, the ultrasonic diagnostic apparatus of the first embodiment is so configured that the stop time of a local destruction high-sound-pressure pulse can be adjusted in the range of 0.01 [sec] to 5 [sec].

In a scan sequence (explained later) executed in the first embodiment, since the target blood vessel is a hepatic artery, the stop time is set at 0.5 [sec]. The transmission range R is set to a value equivalent to three scanning lines and the transmission frequency is set at 2 [MHz].

(Scan Sequence)

Figure 5:
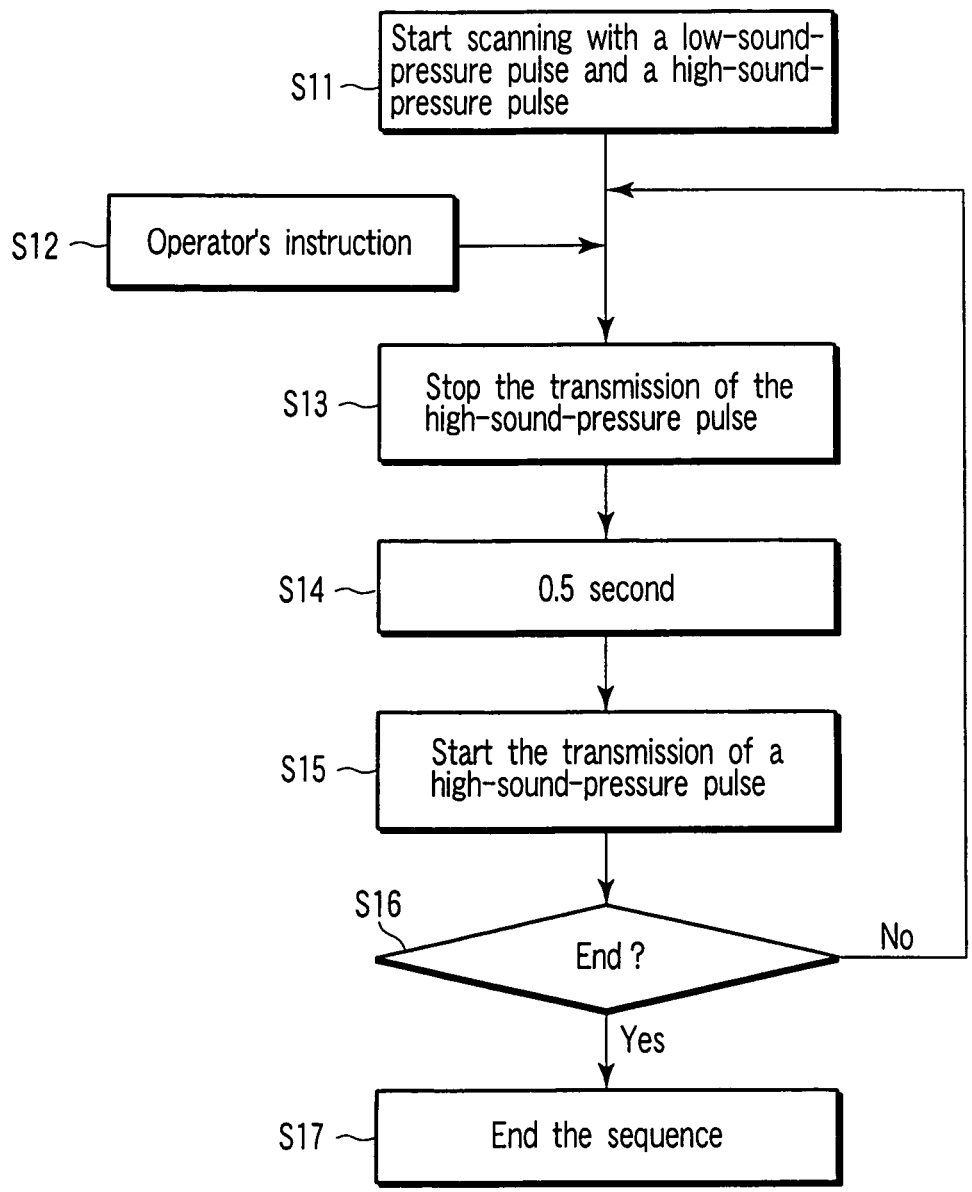
FIG. 5 is a flowchart to help explain a scan sequence in the first embodiment.
Figure 6A:
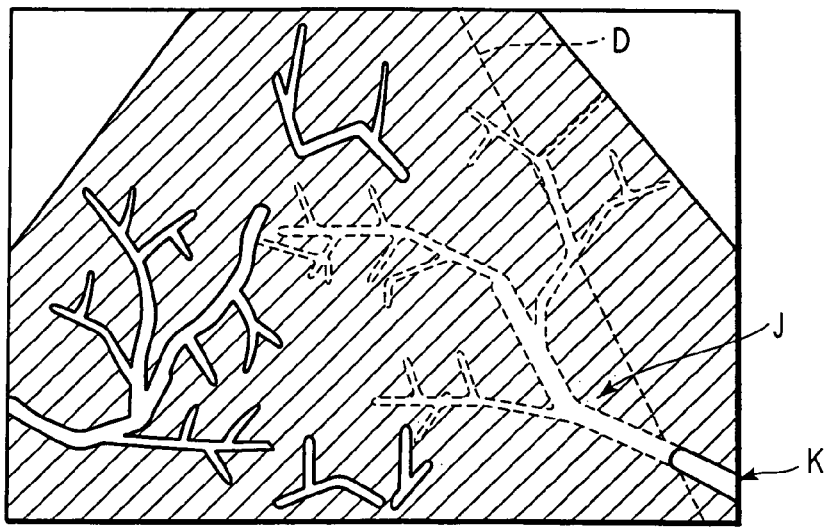
FIG. 6A shows an ultrasonic image illustrating a state where bloodstream information on the main part to peripheral of the target blood vessel has disappeared in the first embodiment.
Figure 6B:
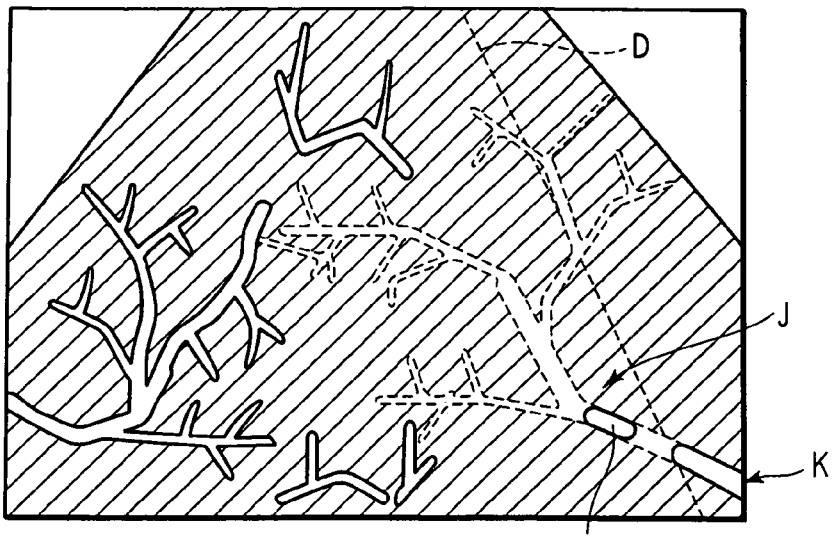
FIG. 6B shows an ultrasonic image illustrating a state where a blob bubble develops in the first embodiment.
Figure 6C:
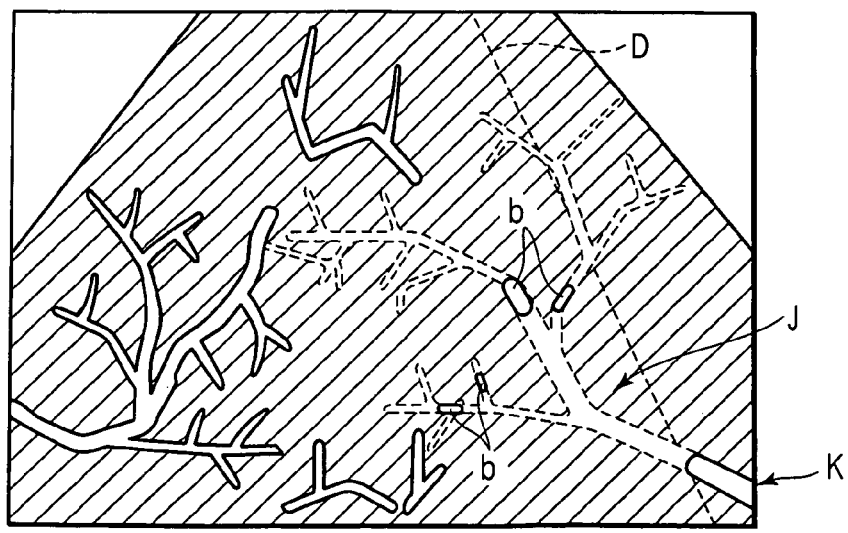
FIG. 6C shows an ultrasonic image illustrating a state where a blob bubble is bifurcated or diluted in the first embodiment.

FIG. 5 is a flowchart to help explain a scan sequence in the first embodiment. FIG. 6A shows an ultrasonic image illustrating a state where bloodstream information on the main part to peripheral of the target blood vessel J has disappeared in the first embodiment. FIG. 6B shows an ultrasonic image illustrating a state where a blob bubble b develops in the first embodiment. FIG. 6C shows an ultrasonic image illustrating a state where a blob bubble b is bifurcated or diluted in the first embodiment.

After finishing the parameter setting, the operator presses the button 13c. Then, the sound pressure in an area A equivalent to three scanning lines with the transmission direction D in the center (hereinafter, referred to as an irradiated area) is switched to a high sound pressure which can practically destroy a bubble. This starts scanning with an ultrasonic pulse in which a low-sound-pressure pulse mixes with a local destruction high-sound-pressure pulse (step S11).

FIG. 6A shows an ultrasonic image at that time. While the local destruction high-sound-pressure pulse is being transmitted, the bubbles existing in the irradiated area A are destroyed by the sound pressure. Therefore, as the time during which the local destruction high-sound-pressure pulse is being transmitted becomes longer, bloodstream information on the main part K to peripheral of the target blood vessel J disappears as shown in FIG. 6A.

Next, the operator presses the button 13c with the desired timing, while looking at the ultrasonic image displayed on the monitor 14 (step S12). Then, the transmission of the local destruction high-sound-pressure pulse stops (step S13). When the transmission of the local destruction high-sound-pressure pulse is at a stop, a low-sound-pressure pulse may be transmitted instead. When the transmission of the local destruction high-sound-pressure pulse has stopped, the bubbles in the target blood vessel J start to flow from the main part K to the downstream and bloodstream information spreads toward the peripheral of the target blood vessel J.

Then, when 0.5 [sec] has passed since the stop of the local destruction high-sound-pressure pulse (step S14), the transmission of the local destruction high-sound-pressure pulse is started again automatically (step S15). This starts again scanning in which a low-sound-pressure pulse mixes with a local destruction high-sound-pressure pulse.

FIG. 6B shows an ultrasonic image at this time. When the transmission of the local destruction high-sound-pressure pulse is started again, the bubbles existing in the irradiated area A are destroyed again. As a result, a part of the bubble in the main part K of the target blood vessel flowed to the downstream during the time (0.5 [sec]) when the transmission of the local destruction high-sound-pressure pulse stopped is disconnected from the bubble on the upstream side of the main part K and flows in the form of a blob to the downstream of the blood vessel.

Then, a bubble b shaped like a blob (hereinafter, referred to as a blob bubble) is bifurcated or diluted according to the shape of the blood vessel. This enables the operator to check a good part or a bad part of the bloodstream from the way the blob bubble is bifurcated or diluted.

Then, when the desired bloodstream information has been obtained (YES in step S16), the scan sequence is completed (step S17). To look at the bloodstream information again (NO in step S16), the operator presses the button 13c with the desired timing, while looking at the ultrasonic image (step S12). Then, the procedure as described above is executed and the operator can check the way the blob bubble b is bifurcated or diluted again.

(Effect of the First Embodiment)

With the ultrasonic diagnostic apparatus of the first embodiment, while a local destruction high-sound-pressure pulse is being transmitted to the main part K of the target blood vessel J, the transmission of the local destruction high-sound-pressure pulse is stopped for 0.5 [sec] according to an instruction given by the operator.

Therefore, when the transmission of the local destruction high-sound-pressure pulse is started again, a blob bubble b is formed on the downstream side of the main part K of the target blood vessel J. Accordingly, the operator can check the state of the bloodstream in the target blood vessel J, looking at the way the blob bubble b is bifurcated or diluted.

The input unit 13 of the first embodiment has the button 13c to specify the timing of stopping the local destruction high-sound-pressure pulse. This reduces the time lag from when the operator specifies timing until the transmission of the local destruction high-sound-pressure pulse actually stops, which makes it possible to obtain bloodstream information at the instant wanted by the operator.

In the first embodiment, the transmission of a local destruction high-sound-pressure pulse has been stopped only once. However, the present invention is not limited to this. Specifically, the number of stops of a local destruction high-sound-pressure pulse and the interval between stops of an local destruction high-sound-pressure pulse may be set freely by the operation of the mouse 13d, keyboard 13e, or the like. In this case, since a plurality of blob bubbles b are formed at specific intervals of time, the operator can see how the state of the bifurcation or dilution of blob bubbles changes as time elapses, looking at the blob bubbles b.

In the first embodiment, the target blood vessel has been assumed to be the hepatic artery. Therefore, the stop time of a local destruction high-sound-pressure pulse has been artificially set at 0.5 [sec] most suitable for the hepatic artery. However, the present invention is not limited to this. For instance, the stop time best suited for the target blood vessel J may be automatically calculated on the basis of the blood velocity detected by the Doppler processing unit 23.

Furthermore, if the transmitting and receiving unit 21 has the function of transmitting and receiving an ultrasonic pulse three-dimensionally and the image generating circuit 24 has the function of generating a three-dimensional image or a two-dimensional projected image from three-dimensional volume data, many pieces of information can be obtained from the three-dimensional volume data received by the transmitting and receiving unit 21. That is, the present invention can be used with three-dimensional representation.

(Second Embodiment)

Next, a second embodiment of the present invention will be explained. In the second embodiment, an explanation of the same configuration and function as those of the first embodiment will be omitted.

Figure 7:
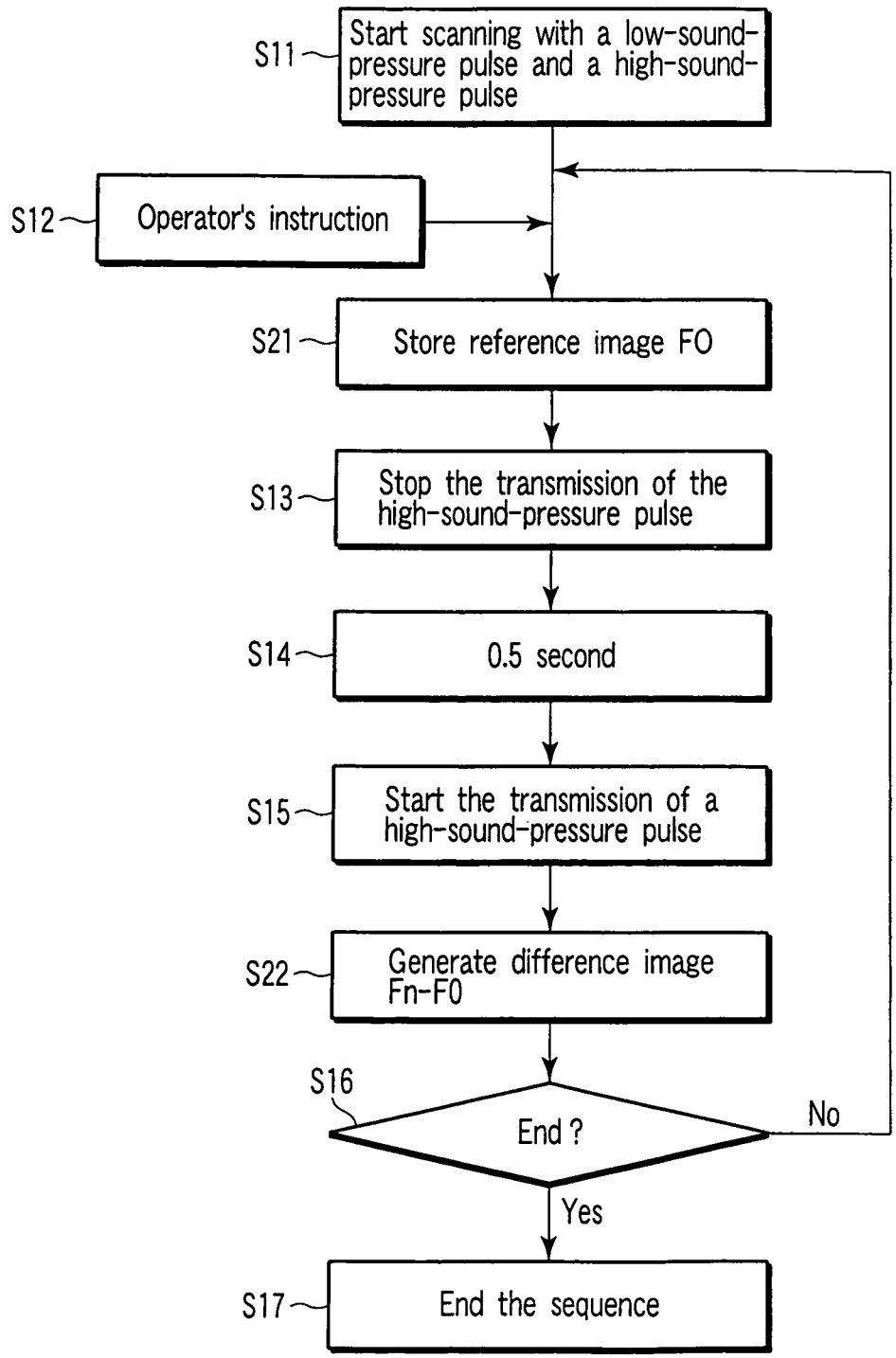
FIG. 7 is a flowchart to help explain a scan sequence in a second embodiment of the present invention.
Figure 8A:
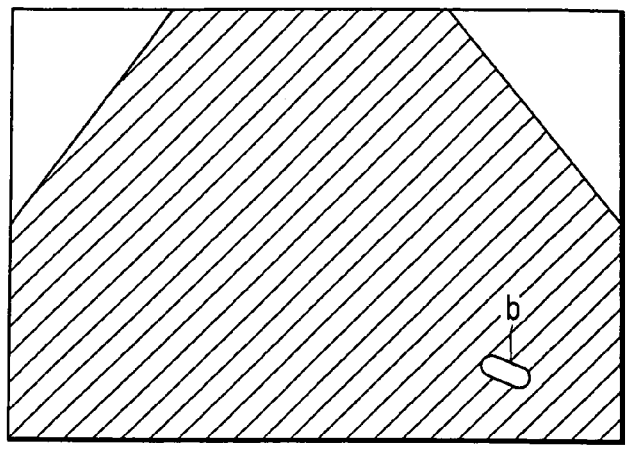
FIG. 8A shows a difference image immediately after the sequence starts in the second embodiment.
Figure 8B:
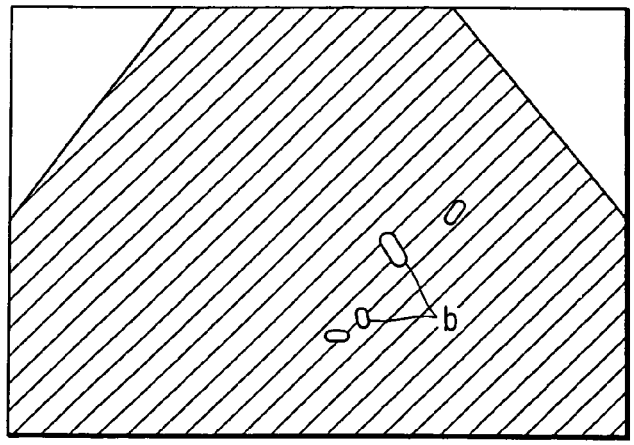
FIG. 8B shows a difference image after a specific time has elapsed since the sequence started in the second embodiment.

FIG. 7 is a flowchart to help explain a scan sequence in the second embodiment. FIG. 8A shows a difference image immediately after the sequence starts in the second embodiment. FIG. 8B shows a difference image after a specific time has elapsed since the sequence started in the second embodiment.

As shown in FIG. 7, a scan sequence of the second embodiment is such that step S21 and step S22 are added to the scan sequence of the first embodiment.

Specifically, in the scan sequence of the second embodiment, when the operator presses the button 13c (step S12), the ultrasonic image generated immediately before that is recorded as a reference image F0 (step S21). As shown in FIG. 6A, the reference image F0 is an ultrasonic image from which the bubbles in the target blood vessel J have disappeared as a result of the transmission of a local destruction high-sound-pressure pulse.

Furthermore, when the transmission of a local destruction high-sound-pressure pulse is started (step S15), a luminance difference operation is performed on ultrasonic images F1, F2, ... generated one after another with respect to the reference image F0 by scanning with a low-sound-pressure pulse. As a result, difference images F1–F0, F2–F0, ... obtained by extracting only blob bubbles b are generated (step S22). As described above, performing a luminance difference operation on the ultrasonic images F1, F2, ... sequentially generated causes bloodstream information on the part excluding the blob bubbles b to disappear from the diagnostic image. This makes it easier for the operator to do a visual check of the way a blob bubble b is bifurcated or diluted.

Moreover, when the reference image F0 and the difference images F1–F0, F2–F0, ... are displayed in difference colors in a superimposing manner on the monitor 14, this makes clear the correspondence of the vascular structure to the way a blob bubble b is bifurcated or diluted. Therefore, it is easier for the operator to check visually at which blood vessel bifurcation the bloodstream has become worse.

Figure 9:
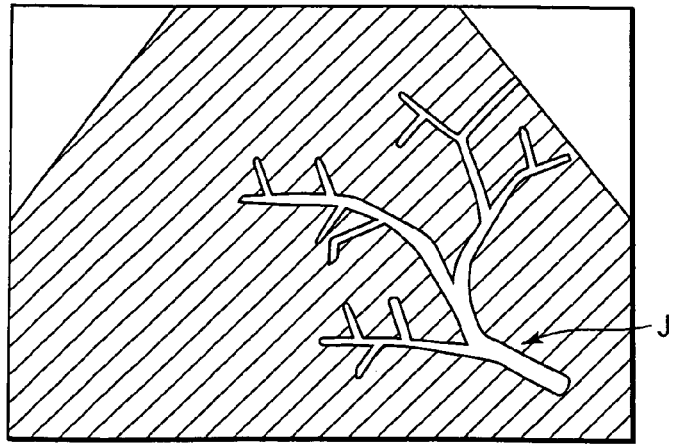
FIG. 9 shows an ultrasonic image obtained by performing a maximum retention operation on difference images in the second embodiment.

It can be assumed that a so-called maximum retention operation is performed on the difference images F1–F0, F2–F0, .... The maximum retention operation is an operation method of comparing the luminances of pixels spatially corresponding to one another in the difference images F1–F0, F2–F0, ... and selectively using the pixels with higher luminance. Since a maximum retention operation is performed on the difference images F1–F0, F2–F0, ..., the track of a blob bubble b is visualized as shown in FIG. 9, presenting a vascular structure. This provides much more information.

Moreover, it can be assumed that an integral operation is performed on the difference images F1–F0, F2–F0, .... The integral operation is an operation method of adding the luminance values of pixels spatially corresponding to one another in the difference images F1–F0, F2–F0, ... and using the luminance resulting from the addition. Since an integral operation is performed on the difference images F1–F0, F2–F0, ..., a density of the blob bubbles b in the blood vessel is represented in luminance, this provides much more information.

Furthermore, it can be assumed that a so-called average operation is performed on the difference images F1–F0, F2–F0, .... The average operation is an operation method of using the average value of the luminance values of pixels spatially corresponding to one another in the difference images F1–F0, F2–F0, .... Performing an average operation on the difference images F1–F0, F2–F0, ... produces a similar effect to that of the integral operation.

(Third Embodiment)

Next, a third embodiment of the present invention will be explained. In the third embodiment, an explanation of the same configuration and function as those of the second embodiment will be omitted.

Figure 10:
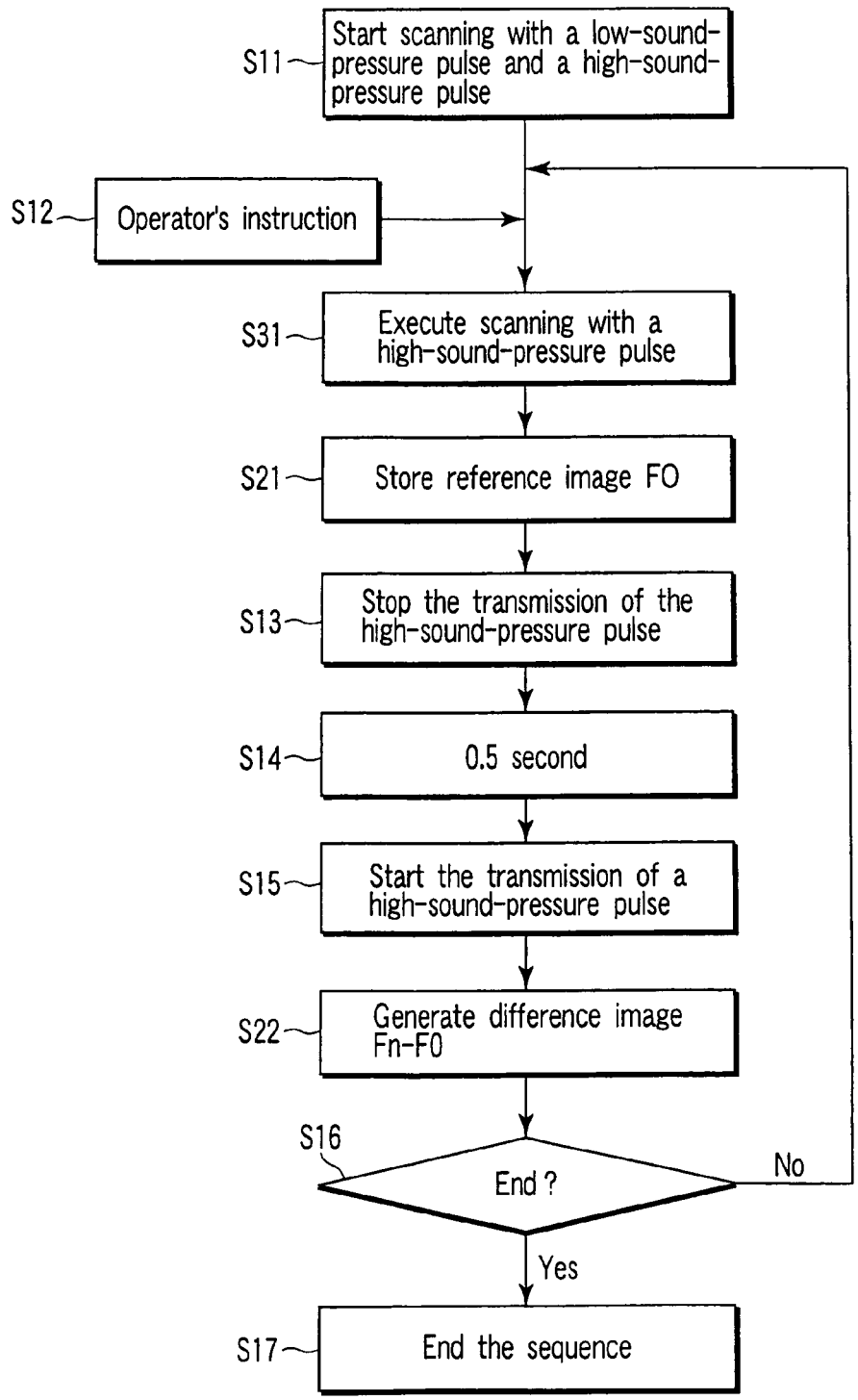
FIG. 10 is a flowchart to help explain a scan sequence in a third embodiment of the present invention.

FIG. 10 is a flowchart to help explain a scan sequence in the third embodiment.

As shown in FIG. 10, a scan sequence of the third embodiment is such that step S31 is added to the scan sequence of the second embodiment.

Specifically, in the scan sequence of the third embodiment, when the operator presses the button 13c (step S12), the subject P is scanned with a general destruction high-sound-pressure pulse (step S31) before the reference image F0 is recorded (step S21), thereby destroying all of the bubbles existing at the scan surface. As a result, even if bubbles have entered the peripheral part of the blood vessel or the tissue, a clear image is obtained without the interference of unnecessary bloodstream information resulting from the entrance.

(Fourth Embodiment)

Next, a fourth embodiment of the present invention will be explained. In the fourth embodiment, an explanation of the same configuration and function as those of the first embodiment will be omitted.

Figure 11:
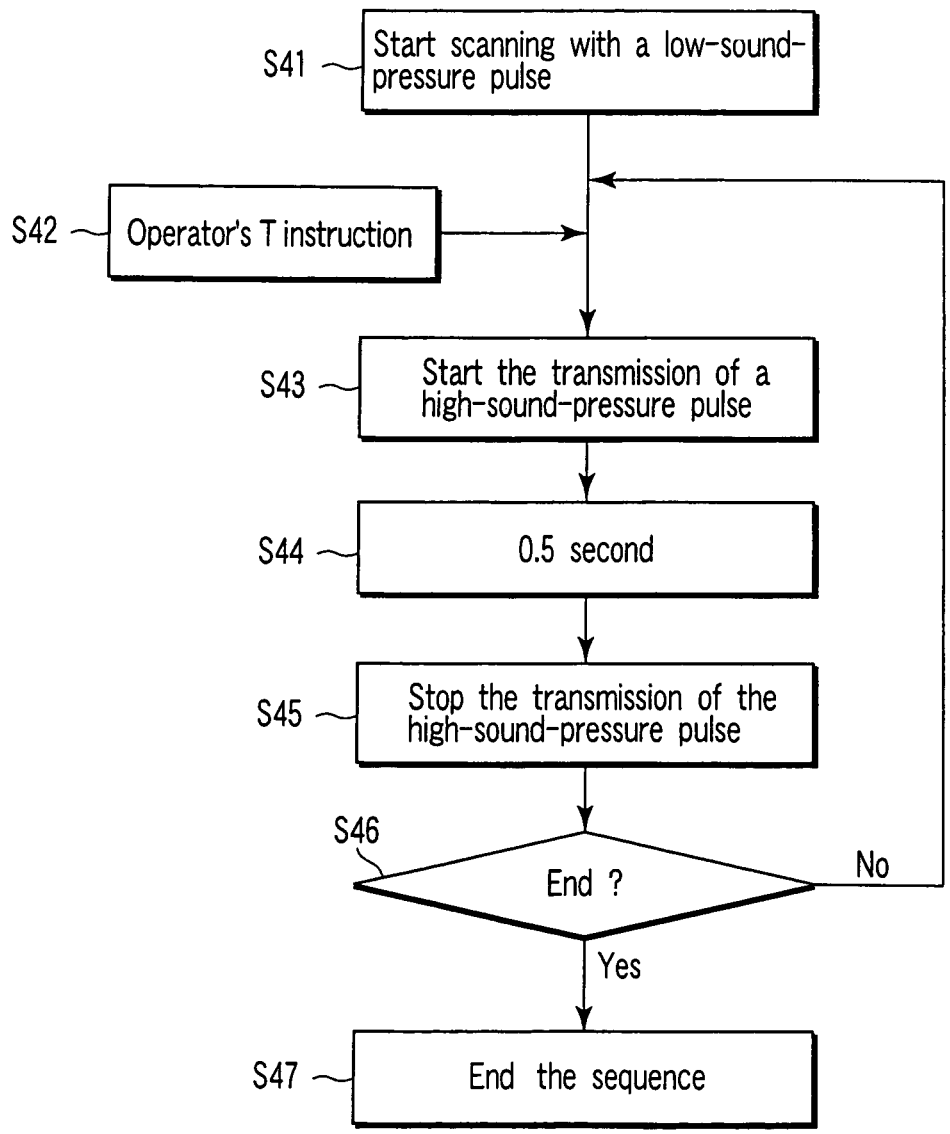
FIG. 11 is a flowchart to help explain a scan sequence in a fourth embodiment of the present invention.
Figure 12A:
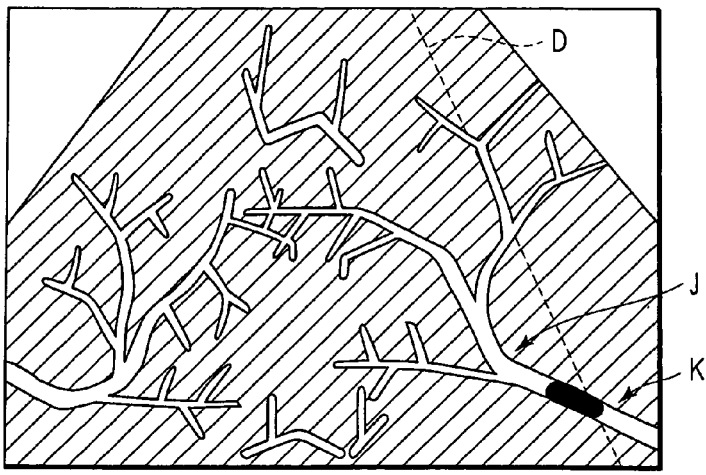
FIG. 12A shows an ultrasonic image illustrating a state where bloodstream information on the main part to downstream of the target blood vessel has disappeared in the fourth embodiment.
Figure 12B:
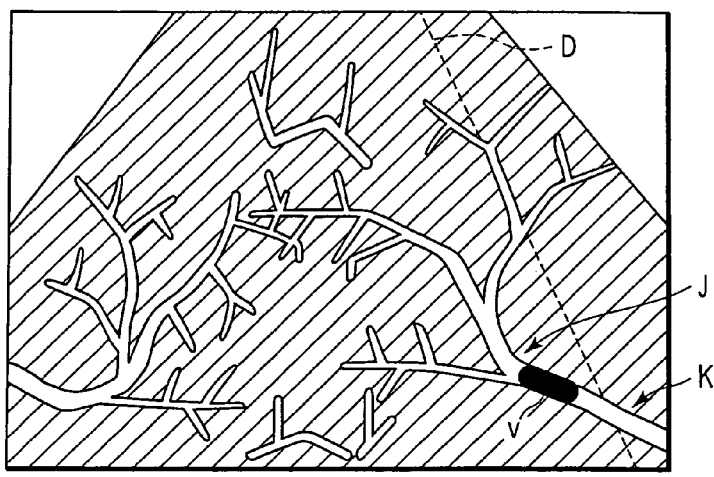
FIG. 12B shows an ultrasonic image illustrating a state where a blob void develops in the fourth embodiment.
Figure 12C:
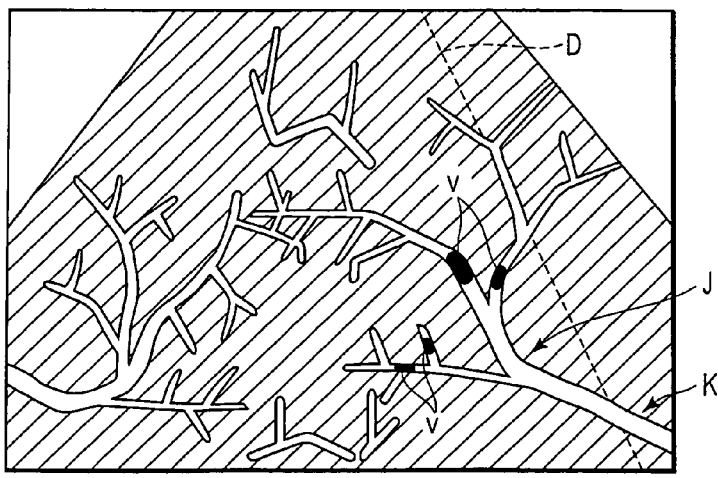
FIG. 12C shows an ultrasonic image illustrating a state where a blob void is bifurcated or diluted in the fourth embodiment.

FIG. 11 is a flowchart to help explain a scan sequence in the fourth embodiment. FIG. 12A shows an ultrasonic image illustrating a state where bloodstream information on the main part K to downstream of the target blood vessel J has disappeared in the fourth embodiment. FIG. 12B shows an ultrasonic image illustrating a state where a blob void v develops in the fourth embodiment. FIG. 12C shows an ultrasonic image illustrating a state where a blob void v is bifurcated or diluted in the fourth embodiment.

In the fourth embodiment, a blob void v is used in place of a blob bubble b. That is, the operator checks the state of the bloodstream, looking at the way a blob void v is bifurcated or diluted. A detailed explanation will be given below.

(Scan Sequence)

After finishing parameter setting to execute a scan sequence, the operator presses the button 13c. Then, the scanning of the subject P is started using only a low-sound-pressure pulse (step S41). In the fourth embodiment, too, the same "next-generation contrast agent" as that in the first embodiment is used. Therefore, as shown in FIG. 3, almost all of the vascular structure at the scanning surface has been drawn on the ultrasonic image obtained by the scanning.

The parameters include the transmission time (arbitrary time) of a local destruction high-sound-pressure pulse, the transmission frequency of the local destruction high-sound-pressure pulse, the transmission direction D of the local destruction high-sound-pressure pulse, and the transmission range D of the local destruction high-sound-pressure pulse. As in the first embodiment, in the fourth embodiment, the transmission time is set at 0.5 [sec], the transmission range R is set to a value equivalent to three scanning lines, and the transmission frequency is set at 2 [MHz].

Then, when a vascular structure has been drawn in an ultrasonic image as a result of the transmission and reception of the low-sound-pressure pulse, the operator presses the button 13c with the desired timing, looking at the vascular structure (step S42). This causes a local destruction high-sound-pressure pulse to be transmitted to the irradiated area A (an area A corresponding to three scanning lines with the transmission direction D in the center) (step S43).

FIG. 12A shows an ultrasonic image at this time. While the local destruction high-sound-pressure pulse is being transmitted, the bubbles existing in the irradiated area A are destroyed by the sound pressure. Therefore, immediately after the local destruction high-sound-pressure pulse is transmitted, a part where bloodstream information has disappeared from the main part K to downstream of the target blood vessel J is formed as shown in FIG. 12A.

Then, after 0.5 [sec] has elapsed since the transmission of the local destruction high-sound-pressure pulse was started (step S44), the transmission of the local destruction high-sound-pressure pulse is automatically stopped (step S45) and scanning is started again with only a low-sound-pressure pulse.

FIG. 12B shows an ultrasonic image at this time. When the transmission of the local destruction high-sound-pressure pulse has stopped, bloodstream information spreads toward the downstream of the main part K of the target blood vessel J. As shown in FIG. 12B, the part where bloodstream information disappeared during the time (0.5 [sec]) when the local destruction high-sound-pressure pulse was being transmitted moves to the downstream of the blood vessel in the form of a blob.

The blob part v (hereinafter, referred to "a blob void") where bloodstream has disappeared is bifurcated or diluted according to the shape of the target blood vessel J as shown in FIG. 12C. This enables the operator to check a good part or a bad part of the bloodstream in the ultrasonic image, looking at the way the blob void v is bifurcated or diluted.

Then, when the desired bloodstream information has been obtained (YES in step S46), the scan sequence is completed (step S47). To look at the bloodstream information again (NO in step S46), the operator presses the button 13c with the desired timing, while looking at the ultrasonic image (step S42). Then, the procedure as described above is executed and the operator can check the way the blob bubble b is bifurcated or diluted again.

With the ultrasonic diagnostic apparatus of the fourth embodiment, while only a low-sound-pressure pulse is being transmitted and received, a local destruction high-sound-pressure pulse is transmitted to the main part K of the target blood vessel J for only 0.5 [sec].

Therefore, when the transmission of the local destruction high-sound-pressure pulse is stopped, a blob void v made up of the disappeared part of the bloodstream information is formed on the downstream side of the main part K of the target blood vessel J. Accordingly, the operator can check the state of the bloodstream in the target blood vessel J as in the first embodiment, looking at the way the blob void v is bifurcated or diluted.

In the fourth embodiment, the trackball 13a, mouse 13d, keyboard 13e, or touch command screen has been used as means for setting the irradiated area A of the local destruction high-sound-pressure pulse. However, this invention is not limited to this, as long as the operator can operate the means easily, looking at the diagnostic image.

This invention is not limited to the above embodiments and may be embodied by modifying the component elements without departing from the spirit or essential character thereof. In addition, various inventions may be formed by combining suitably a plurality of component elements disclosed in the embodiments. For example, some components may be removed from all of the component elements constituting the embodiments. Furthermore, component elements used in two or more embodiments may be combined suitably.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic diagnostic apparatus which obtains a diagnostic image by scanning with an ultrasonic wave on a predetermined scan plane of a subject to whom contrast agent bubbles have been given, the ultrasonic diagnostic apparatus comprising:

an ultrasonic probe configured to be brought into contact with the subject;

a transmitting and receiving section which transmits and receives, via the ultrasonic probe, on the predetermined scan plane, a first ultrasonic wave having a first sound pressure that does not substantially destroy the contrast agent bubbles and that is used for obtaining a blood-stream circulating image, and which transmits, via the ultrasonic probe, to a first area on the predetermined scan plane, a second ultrasonic wave having a second sound pressure that destroys the contrast agent bubbles;

a doppler scanner configured to execute a doppler scan;

a control section which controls the transmitting and receiving section to execute the transmission of the second ultrasonic wave to the first area a first plurality of times for a first period to destroy the contrast agent bubbles in the first area, stop the transmission of the second ultrasonic wave for a second period no longer than the first period to cause the contrast agent bubbles to flow into a second area downstream of the first area, execute the transmission of the second ultrasonic wave to only the first area a second plurality of times for a third period after the second period to form a blob bubble in the second area, execute the transmission of the first ultrasonic wave to the predetermined scan plane after the third period, and change a period in which the transmission of the second ultrasonic wave is stopped according to a measured doppler velocity from the doppler scan;

an image generating section which generates first images on the basis of a plurality of received signals obtained by the transmission and reception of the first ultrasonic wave, the first images being images in which the blob bubble is visualized; and a display section which displays the first images.

2. The ultrasonic diagnostic apparatus according to claim 1, wherein the control section is configured to stop the transmission of the second ultrasonic wave for the second period, the second period falling within a period during which a discontinuous part of the contrast agent bubble formed by the plurality of transmissions of the second ultrasonic wave is seen in the first images and remains in the first area.

3. The ultrasonic diagnostic apparatus according to claim 2, further comprising a setting section configured to set the second period to 0.01 seconds to 5 seconds.

4. The ultrasonic diagnostic apparatus according to claim 2, further comprising a setting section which sets the second period and the number of executions or pauses of the plurality of transmissions of the second ultrasonic wave.

5. The ultrasonic diagnostic apparatus according to claim 2, further comprising an image processing section which generates a plurality of difference images, each difference image being obtained by using the first images and a second image acquired before the first period.

6. The ultrasonic diagnostic apparatus according to claim 5, wherein the image processing section, using the plurality of difference images, is configured to perform at least one of a maximum retention operation, a minimum retention operation, an integral operation, and an average operation in luminance on each of the positions corresponding to one another on the individual difference images.

7. The ultrasonic diagnostic apparatus according to claim 5, wherein the display section displays at least one of the first images and the difference images in a superimposing manner.

8. The ultrasonic diagnostic apparatus according to claim 7, wherein the display section displays at least one of the first images and the difference images in different colors.

9. The ultrasonic diagnostic apparatus according to claim 1, further comprising a setting section for setting a range to which the second ultrasonic wave is transmitted.

10. The ultrasonic diagnostic apparatus according to claim 1, wherein the transmitting and receiving section transmits a third ultrasonic wave which has a sound pressure that destroys the contrast agent bubble to the whole of the first area before transmitting the second ultrasonic wave.

11. The ultrasonic diagnostic apparatus according to claim 10, wherein the control section controls the transmitting and receiving section of the timing of the transmission of the third ultrasonic wave.

12. The ultrasonic diagnostic apparatus according to claim 1, wherein the transmitting and receiving section executes the transmission and reception of the first ultrasonic wave and the second transmission three-dimensionally a plurality of times, and the image generating section generates the first images as a plurality of three-dimensional images or two-dimensional projected images.

13. An ultrasonic diagnostic method of obtaining a diagnostic image by scanning with an ultrasonic wave on a predetermined scan plane of a subject to whom contrast agent bubbles have been given, the ultrasonic diagnostic method comprising:

transmitting, a first plurality of times to a first area on the predetermined scan plane, a first ultrasonic wave for a first period, the first ultrasonic wave having a first sound pressure that substantially destroys the contrast agent bubble to destroy the contrast agent bubbles;

executing a doppler scan;

stopping the transmission of the first ultrasonic wave for a second period no longer than the first period to cause the contrast agent bubbles to flow into a second area downstream of the first area;

transmitting, a second plurality of times, the first ultrasonic wave to only the first area for a third period after the second period to form a blob bubble in the second area;

transmitting, to the predetermined scan plane, a second ultrasonic wave having a sound pressure that does not destroy the contrast agent bubbles, after the third period, and changing a period in which the transmission of the second ultrasonic wave is stopped according to a measured doppler velocity from the doppler scan;

generating first images on the basis of a plurality of received signals obtained by the transmission and reception of the second ultrasonic wave, the first images being images in which the blob bubble is visualized; and displaying the first images.

14. The ultrasonic diagnostic method according to claim 13, the second period falling within a period during which a discontinuous part of the contrast agent bubble formed by the transmission of the first ultrasonic wave is seen in the first images and remains in the first area.

15. The ultrasonic diagnostic method according to claim 14, wherein the second period is 0.01 seconds to 5 seconds.

16. The ultrasonic diagnostic method according to claim 14, wherein the second period and the number of executions or pauses of the transmission of the first ultrasonic wave is set arbitrarily.

17. The ultrasonic diagnostic method according to claim 14, wherein a plurality of difference images are generated, each difference image being obtained by using the first images and a second image acquired before the first period.

18. The ultrasonic diagnostic method according to claim 17, further comprising performing at least one of a maximum retention operation, a minimum retention operation, an integral operation, and an average operation in luminance on each of the positions corresponding to one another on the individual difference images, using the plurality of difference images.

19. The ultrasonic diagnostic method according to claim 17, further comprising displaying at least one of the first images and the difference images in a superimposing manner.

20. The ultrasonic diagnostic method according to claim 19, wherein the displaying step comprises displaying at least one of the first image and the difference images in different colors.

21. The ultrasonic diagnostic method according to claim 13, wherein the range to which the second ultrasonic wave is transmitted is set arbitrarily.

22. The ultrasonic diagnostic method according to claim 13, further comprising transmitting a third ultrasonic wave which has a sound pressure that destroys the contrast agent bubble to the whole of the first area before the second ultrasonic wave is transmitted.

23. The ultrasonic diagnostic method according to claim 22, further comprising setting the timing of the transmission of the third ultrasonic wave arbitrarily.

24. The ultrasonic diagnostic method according to claim 13, wherein the transmission and reception of the first ultrasonic wave and the transmission of the second ultrasonic wave are executed three-dimensionally a plurality of times, and a plurality of three-dimensional images or two-dimensional projected images are generated as the first images.

25. The ultrasonic diagnostic apparatus according to claim 1, wherein the control section controls the transmitting and receiving section to execute the transmission of the first ultrasonic wave to the first area a plurality of times for the second period.

26. The ultrasonic diagnostic apparatus according to claim 1, wherein the control section controls a length of the first period based on a bloodstream velocity measured by a doppler mode from the doppler scan.

27. The ultrasonic diagnostic apparatus according to claim 1, wherein the control section controls the transmitting and receiving section such that the first period is shortened as a bloodstream velocity increases.

28. The ultrasonic diagnostic apparatus according to claim 25, wherein, in response to a predetermined operation in the first period, the control section controls the transmitting and receiving section to execute the transmission of the first ultrasonic wave to the first area a plurality of times for the second period and execute the transmission of the second ultrasonic wave to the first area a plurality of times for the third period automatically.

* * * * *